(12) United States Patent
Cottingham et al.

(10) Patent No.: US 8,975,226 B2
(45) Date of Patent: Mar. 10, 2015

(54) PHARMACEUTICAL PREPARATION COMPRISING RECOMBINANT HCG

(75) Inventors: Ian Cottingham, St. Prex (CH); Daniel Plaksin, St. Prex (CH); Richard Boyd White, San Diego, CA (US)

(73) Assignee: Ferring B.V., Hoofddorp (NL)

( * ) Notice: Subject to any disclaimer, the term of this patent is extended or adjusted under 35 U.S.C. 154(b) by 50 days.

(21) Appl. No.: 13/500,274

(22) PCT Filed: Oct. 4, 2010

(86) PCT No.: PCT/GB2010/001854
§ 371 (c)(1),
(2), (4) Date: Sep. 27, 2012

(87) PCT Pub. No.: WO2011/042688
PCT Pub. Date: Apr. 14, 2011

(65) Prior Publication Data
US 2013/0023476 A1 Jan. 24, 2013

(30) Foreign Application Priority Data
Oct. 5, 2009 (EP) .................................... 09252360

(51) Int. Cl.
*A61K 38/24* (2006.01)
(52) U.S. Cl.
USPC ......................................... 514/9.9; 435/69.4
(58) Field of Classification Search
None
See application file for complete search history.

(56) References Cited

U.S. PATENT DOCUMENTS

| | | | |
|---|---|---|---|
| 5,929,028 A * | 7/1999 | Skrabanja et al. ........... | 514/10.1 |
| 2005/0085412 A1 | 4/2005 | Loumaye et al. | |
| 2008/0226681 A1 * | 9/2008 | Goletz et al. ............... | 424/278.1 |
| 2011/0105398 A1 | 5/2011 | Cottingham et al. | |

FOREIGN PATENT DOCUMENTS

| | | |
|---|---|---|
| WO | WO 88/10270 | 12/1988 |
| WO | WO 03/035686 | 5/2003 |
| WO | WO03/038100 | 5/2003 |
| WO | WO2004/105788 | 12/2004 |
| WO | WO2005/076013 | 8/2005 |
| WO | WO2005/080585 | 9/2005 |
| WO | WO2009/127826 | 10/2009 |

OTHER PUBLICATIONS

Structure and location of the O-glycosidic carbohydrate units of human chorionic gonadotropin. Kessler MJ, Mise T, Ghai RD, Bahl OP. J Biol Chem. Aug. 25, 1979;254(16):7909-14.*
Kessler et al (J Biol Chem. vol. 25, No. 16, Aug. 25, 1979, pp. 7909-7914).*
Hard et al., "The Carbohydrate Chains of the [beta] Subunit of Human Chorionic Gonadotropin Produced by the Choriocarcinoma Cell Line BeWo. Novel O-linked and Novel Bisecting-G1cNAc-Containing N-linked Carbohydrates", *European Journal of Biochemistry* DE, 1992, 205(2), 1992, 785-798.
International Search Report dated Jan. 31, 2011 for International Appln. No. PCT/GB2010/001854 (4 pgs.).
Amoresano et al., "Structural characterisation of human recombinant glycohormones follitropin, lutropin and choriogonadotropin expressed in Chinese hamster ovary cells," Eur J Biochem., 1996, 242, 608-618.
Andersen et al., FSH Isoform Composition of Commercial Gonadotrophin Preparations: a Neglected Aspect? *Reprod. Biomed. Online*, 2004, 9(2), 231-236.
Arey et al., "Induction of promiscuous G protein coupling of the follicle-stimulating hormone (FSH) receptor: a novel mechanism for transducing pleiotropic actions of FSH isoforms", *Mol. Endocrinol.*, 1997, 11(5), 517-26.
Avis, K. E., "Parenteral Preparations—History, Administration, Components, Production, Quality Control, Packaging, Labeling", *Remington's Pharmaceutical Sciences*, fifteenth edition, 1975, 1461-1487.
Baenziger, et al., "Pituitary glycoprotein hormone oligosaccharides: structure, synthesis and function of the asparagine-linked oligosaccharides on lutropin, follitropin and thyrotropin", *Biochim. Biophys. Acta.*, 1988, 947(2), 287-306.
Bassett et al., "Continued Improvements in the Quality and Consistency of Follitropin Alfa, Recombinant Human FSH", *Reprod. Biomed. Online*, 2005, 10(2), 169-177.
Combarnous, Y., "Structure et relations structure-activité des hormones folliculo-stimulantes recombinantes humaines", *Médecine/Sciences*, 1999, 15, 167-74 (with English translation).
Dalpathado et al., "Comparative glycomics of the glycoprotein follicle stimulating hormone: glycopeptide analysis of isolates from two mammalian species", *Biochem.*, 2006, 45(28), 8665-73.
Damián-Matsumura et al., "Oestrogens regulate pituitary alpha2,3-sialyltransferase messenger ribonucleic acid levels in the female rat", *J. Mol. Endocrinol.*, 1999, 23(2), 153-65.
D'Antonio et al., "Biological Characterization of Recombinant Human Follicle Stimulating Hormone Isoforms", *Human Reproduction*, 1999, 14, 1160-1167.
de Leeuw et al., "Structure-function relationship of recombinant follicle stimulating hormone (Puregon®)", *Mol. Hum. Reprod.*, 1996, 2, 361-69.
Deardoff, D. L., "Isotonic Solutions—Freezing Point, Calculations, Tonicity Testing, Methods", *Remington's Pharmaceutical Sciences*, fifteenth edition, 1975, 1405-1412.
Dias et al., "Structural biology of human follitropin and its receptor", *Arch. Med. Res.*, 2001, 32(6), 510-19.

(Continued)

*Primary Examiner* — Brian J Gangle
*Assistant Examiner* — Andrea McCollum
(74) *Attorney, Agent, or Firm* — Fish & Richardson P.C.

(57) ABSTRACT

The present disclosure describes recombinant human chorionic gonadotropin (hCG) and methods for the production thereof. The recombinant hCG can include α2,3, α2,6, and, optionally, α2,8 sialylation. The recombinant hCG can be produced in a human cell line such as a PER.C6® cell line.

25 Claims, 5 Drawing Sheets

(56) References Cited

OTHER PUBLICATIONS

Expert Declaration (Exhibit No. 52) and Curriculum Vitae (Exhibit No. 52a) of Yves Combarnous dated Aug. 28, 2009 (27 pgs.).
Fiddes et al., "Isolation, Cloning and Sequence Analysis of the cDNA for the Alpha-Subunit of Human Chorionic Gonadotropin", Nature, 1979, 281, 351-356.
Fiddes et al., "The cDNA for the Beta-Subunit of Human Chorionic Gonadotropin Suggests Evolution of a Gene by Readthrough into the 3'-Untranslated Region", Nature, 1980, 286, 684-387.
Flack et al., "Increased biological activity due to basic isoforms in recombinant human follicle-stimulating hormone produced in a human cell line", *J. Clin. Endocrinol. Metab.*, 1994, 3(79), 756-60.
Fox et al., "Three-dimensional structure of human follicle-stimulating hormone", *Mol. Endocrinol.* 2001, 15(3), 378-89.
Grabenhorst et al., "Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal(beta 1-4)GlcNAc(beta 1-2)Man(alpha 1-3)-branch of diantennary oligosaccharides from secreted recombinant beta-trace protein", *Eur. J Biochem.*, 1995, 232(3), 718-25.
Green, E. D. et al., "Asparagine-linked oligosaccharides on lutropin, follitropin, and thyrotropin. II. Distributions of sulfated and sialylated oligosaccharides on bovine, ovine, and human pituitary glycoprotein hormones", *J. Biol. Chem.*, 1988, 263(1), 36-44.
Grundmann et al., "Complete cDNA sequence encoding human beta-galactoside alpha-2,6-sialyltransferase", *Nucleic Acids Res.*, 1990, 18(3), 667.
Harvey, S. C., "Cardiovascular Drugs—Antihypertensive and Hypotensive Drugs, Peripheral Vasodilators, Coronary Drugs, Cardiac Glycosides, Antiarrhythmic Drugs, Drugs Affecting Blood Lipids, Miscellaneous Drugs", *Remington's Pharmaceutical Sciences*, fifteenth edition, 1975, 807-820.
Harvey, S. C., "Sympathomimetic Drugs", *Remington's Pharmaceutical Sciences*, fifteenth edition, 1975, 780-797.
Horseman et al., "A biological, immunological and physic-chemical comparison of the current clinical batches of the recombinant FSH preparations Gonal-F and Puregon", *Hum. Reprod.*, 2000, 15(9), 1898-1902.
Howles, C. M., "Genetic engineering of human FSH (Gonal-F®)", Hum. Reprod. Update, 1996, 2(2), 172-91.
International Search Report dated Jun. 30, 2009 for International Appl. No. PCT/GB2009/000978 (8 pgs.).
Jones et al., "High level expression of recombinant IgG in the human cell line Per.C6", Biotechnol. Progress, 2003, 19, 163-68.
Kagawa et al., "Comparative Study of the Asparagine-linked Sugar Chains of Natural Human Interferon-beta 1 and Recombinant Human Interferon-beta 1 Produced by Three Different Mammalian Cells", *J. Biol. Chem.*, 1988, 263(33), 17508-17515.
Keene et al., "Expression of Biologically active Human Follitropin in Chinese Hamster Ovary Cells", *J. Biol. Chem.*, 1989, 264(9), 4769-75.
Kitagawa et al., Cloning of a Novel α2,3-Sialyltransferase that Sialylates Glycoprotein and Glycolipid Carbohydrate Groups, *J. Biol. Chem.*, 1994, 269(2), 1394-1401.
Lee et al., "Alteration of terminal glycosylation sequences on N-linked oligosaccharides of Chinese hamster ovary cells by expression of beta-galactoside alpha 2,6-sialyltransferase", *J. Biol. Chem.*, 1989, 264(23), 13848-55.
Lowry et al., "Protein Measurement with the Folin Phenol Reagent", *J. Biol. Chem.*, 1951, 193(1), 265-75.
Lowry et al., "Purification of Anterior Pituitary and Hypothalamic Hormones", *Clin. Pathol. Suppl. (Assoc. Clin. Pathol.)*, 1976, 16-21.
Olijve et al., "Molecular biology and biochemistry of human recombinant follicle stimulating hormone (Puregon®)", *Mol. Hum. Reprod.*, 1996, 2(5), 371-82.
Otto et al., "Sialylated complex-type N-Glycans enhance the signalling activity of soluble intercellular adhesion molecule-1 in mouse astrocytes," *J Biol. Chem.*, 2004, 270(34), 35201-35209.

Pierce et al., "Glycoprotein hormones: structure and function", *Ann. Rev. Biochem.*, 1981, 50, 465-95.
Pricer et al., "The binding of desialylated glycoproteins by plasma membranes of rat liver", *J. Biol. Chem.*, 1971, 246(15), 4825-33.
Rathnam et al., "Primary amino acid sequence of follicle-stimulating hormone from human pituitary glands. I. alpha subunit", *J. Biol. Chem.*, 1975, 250(17), 6735-46.
Regoeczi et al., "Elimination of asialofetuin and asialoorosomucoid by the intact rat. Quantitative aspects of the hepatic clearance mechanism", *Biochim. Biophys. Acta.*, 1978, 541(3), 372-84.
Royle et al., "Detailed Structural Analysis of N-Glycans Released from Glycoproteins in SDS-PAGE Gel Bands Using HPLC Combined with Exoglycosidase Array Digestions," Methods in Molecular Biology: *Glycobiology protocols*, 2006, 347: 125-144.
Ryan et al., "Structure-function relationships of gonadotropins", *Recent Prog Horm Res.*, 1987, 43, 383-429.
Saxena et al., "Amino acid sequence of the beta subunit of follicle-stimulating hormone from human pituitary glands", *J. Biol. Chem.*, 1976, 251(4), 993-1005.
Stanton et al., "Application of a sensitive HPLC-based fluorometric assay to determine the sialic acid content of human gonadotropin isoforms," *J. Biochem. Biophys. Methods*, 1995, 30:37-48.
Steelman et al., "Assay of the Follicle Stimulating Hormone Based on the Augmentation with Human Chorionic Gonadotropin", *Endocrinology*, 1953 53(6), 604-616.
Steer et al., "Studies on a mammalian hepatic binding protein specific for asialoglycoproteins. Evidence for receptor recycling in isolated rat hepatocytes", *J. Biol. Chem.*, 1980, 255(7), 3008-13.
Svensson et al., "Organization of the Beta-galactoside Alpha 2,6-sialyltransferase Gene. Evidence for the Transcriptional Regulation of Terminal Glycosylation", *J. Biol. Chem.*, 1990, 265(34):20863-20868.
Swinyard, "Respiratory Drugs—Stimulants, Expectorants, Antitussives, Gases", *Remington's Pharmaceutical Sciences*, fifteenth edition, 1975, 798-806.
Takeuchi et al., "Comparative Study of the Asparagine-linked Sugar Chains of Human Erythropoietins Purified from Urine and the Culture Medium of Recombinant Chinese Hamster Ovary Cells", *J. Biol. Chem.*, 1988, 263(8), 3657-3663.
Timossi et al., "A naturally occurring basically charged human follicle-stimulating hormone (FSH) variant inhibits FSH-induced androgen aromatization and tissue-type plasminogen activator enzyme activity in vitro", *Neuroendocrinol.*, 1998, 67(3), 153-63.
Timossi et al., "Differential effects of the charge variants of human follicle-stimulating hormone", *J. Endocrinol.*, 2000, 165(2), 193-205.
Ulloa-Aguirre et al., "Biological characterization of the naturally occurring analogues of intrapituitary human follicle stimulating hormone", *Hum. Reprod.*, 1992, 7(1), 23-30.
Ulloa-Aguirre et al., "Endocrine regulation of gonadotropin glycosylation", *Arch. Med. Res.*, 2001, 32(6), 520-32.
Ulloa-Aguirre et al., "Immunological and biological potencies of the different molecular species of gonadotrophins", *Hum. Reprod.*, 1988, 3, 491-501.
Ulloa-Aguirre et al., "Follicle-stimulating Isohormones: Characterization and Physiological Relevance", *Endocr. Rev.*, 1995, 16(6), 765-87.
Ulloa-Aguirre et al., "Impact of Carbohydrate Heterogeneity in Function of Follicle-stimulating Hormone: Studies Derived from in vitro and in vivo models", *Biol. Reprod.*, 2003, 69(2), 379-389.
Van Lenten et al., "The binding of desialylated glycoproteins by plasma membranes of rat liver. Development of a quantitative inhibition assay", *J. Biol. Chem.*, 1972, 247(14), 4633-40.
Wide et al., "Change in electrophoretic mobility of human follicle-stimulating hormone in serum after administration of gonadotropin-releasing hormone", *J. Clin. Endocrinol. Metab.*, 1990, 70, 271-76.
Wide et al., "More basic forms of both human follicle-stimulating hormone and luteinizing hormone in serum at midcycle compared with the follicular or luteal phase", *J. Clin. Endocrinol. Metab.*, 1993, 76, 885-89.

(56) References Cited

OTHER PUBLICATIONS

Wide et al., "Sulfonation and sialylation of gonadotropins in women during the menstrual cycle, after menopause, and with polycystic ovarian syndrome and in men", *J. Clin. Endocrinol. Metab.*, 2007, 92(11), 4410-17.

Zambrano et al., "Receptor binding activity and in vitro biological activity of the human FSH charge isoforms as disclosed by heterologous and homologous assay systems: Implications for the structure-function relationship of the FSH variants", *Endocrine*, 1999, 10(2), 113-21.

Zhang et al., "Stable expression of human alpha-2,6-sialyltransferase in Chinese hamster ovary cells: functional consequences for human erythropoietin expression and bioactivity", *Biochim. Biophys. Acta.*, 1998, 1425(3), 441-52.

* cited by examiner

PHARMACEUTICAL PREPARATION COMPRISING RECOMBINANT HCG

CROSS-REFERENCE TO RELATED APPLICATIONS

This application is a national phase application under 35 U.S.C. 371 of PCT International Application No. PCT/GB2010/001854, filed on Oct. 4, 2010, which claims the benefit of European Patent Application No. 09252360.4, filed on Oct. 5, 2009.

FIELD

The present invention relates to gonadotrophins for use in the treatment of infertility. In particular it relates to human chorionic gonadotrophin (hCG).

BACKGROUND

The gonadotrophins are a group of heterodimeric glycoprotein hormones which regulate gonadal function in the male and female. They include follicle stimulating hormone (FSH), luteinising hormone (LH) and chorionic gonadotrophin (CG).

Human chorionic gonadotrophin (hCG) is naturally secreted by the anterior pituitary gland and functions to support follicular development and ovulation. hCG comprises a 92 amino acid alpha sub-unit, also common to the other glycoprotein hormones LH and FSH, and a 145 amino acid beta sub-unit unique to hCG, which dictates the hormone specificity. Each sub-unit is post translationally modified by the addition of complex carbohydrate residues. The alpha sub-unit contains 2-N-linked glycosolation sites at amino acids 52 and 78 and the beta sub-unit contains 2-N-linked glycosolation sites at amino acids 13 and 30 and four O-linked glycosylation sites at amino acids 121, 127, 132 and 138.

hCG extracted from the urine of pregnant women [CHORAGON® (Ferring)] has been used for many years in infertility treatment. The production of hCG extracted from urine involves the collection and processing of large amounts of urine. A recombinant version of hCG, OVITRELLE® (Serono), is available. This is expressed in Chinese hamster ovary (CHO) cells. The known recombinant hCG product has a different pharmacokinetic profile to hCG produced from humane urine. It is desirable to have an hCG product that more closely replicates or mimics the pharmacokinetic profile of the product produced from human urine.

There is considerable heterogeneity associated with hCG preparations which relates to differences in the amounts of various isoforms present. Individual hCG isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural hCG is highly complex. The glycans in naturally derived pituitary hCG can contain a wide range of structures that can include combinations of bi-, tri- and tetra-antennary glycans. The glycans can carry further modifications: core fucosylation, bisecting glucosamine, chains extended with acetyl lactosamine, partial or complete sialylation, sialylation with $\alpha 2,3$ and $\alpha 2,6$ linkages, and sulphated galactosamine substituted for galactose. Furthermore, there are differences between the distributions of glycan structures at the individual glycosylation sites.

The glycosylation of recombinant hCG ("rhCG") products reflects the range of glycosyl-transferases present in the host cell line. The existing rhCG product, OVITRELLE®, is derived from engineered Chinese hamster ovary cells (CHO cells). The range of glycan modifications in CHO derived rhCG are more limited than those found on the natural products, derived from urine. Examples of the reduced glycan heterogeneity found in CHO derived rhCG include a lack of bisecting glucosamine and a reduced content of core fucosylation and acetyl lactosamine extensions. In addition, CHO cells are only able to add sialic acid using the $\alpha 2,3$ linkage (Kagawa et al., 1988, Takeuchi et al., 1988, Svensson et al., 1990). This is different from naturally produced hCG which contains glycans with a mixture of $\alpha 2,3$ and $\alpha 2,6$-linked sialic acid.

It has been demonstrated that a recombinant FSH preparation (Organon) differs in the amounts of FSH with an isoelectric point (pI) of below 4 (considered the acidic isoforms) when compared to pituitary, serum or post-menopausal urine FSH (Ulloa-Aguirre et al. 1995). The amount of acidic isoforms in the urinary preparations of FSH was much higher as compared to the recombinant products, GONAL-F® (Serono) and PUREGON® (Organon) (Andersen et al. 2004). This must reflect a lower molar content of sialic acid in rFSH since the content of negatively-charged glycan modified with sulphate is low in FSH. The lower sialic acid content, compared to natural FSH, is a feature of both commercially available FSH products and therefore must reflect a limitation in the manufacturing process (Bassett and Driebergen, 2005). The circulatory life-time of FSH has been documented for materials from a variety of sources. Some of these materials have been fractionated on the basis of overall molecular charge, as characterised by their pI, in which more acid equates to a higher negative charge. The major contributor to overall molecular charge is the total sialic content of each FSH molecule. For instance, rFSH (Organon) has a sialic acid content of around 8 mol/mol, whereas urine-derived FSH has a higher sialic acid content (de Leeuw et al. 1996). The corresponding plasma clearance rates in the rat are 0.34 and 0.14 ml/min (Ulloa-Aguirre et al. 2003). In another example where a sample of recombinant FSH was split into high and low pI fractions, the in vivo potency of the high pI (lower sialic acid content) fraction was decreased and it had a shorter plasma half-life (D'Antonio et al. 1999). The applicants have found that, similar to FSH, the known, CHO derived, recombinant hCG product (e.g. OVITRELLE®) also has a lower amount of hCG with an isoelectric point (pI) of below 4 (considered the acidic isoforms) than urinary hCG, also reflecting a lower sialic acid content of the known rhCG product compared to urinary hCG.

The total sialic acid content of hCG and rhCG is not directly comparable since sialic acids are commonly linked in two ways. Pituitary/serum/urinary hCG contain both $\alpha 2,3$ and $\alpha 2,6$-linked sialic acid, with a predominance of the former. However, CHO cell derived recombinants only contain $\alpha 2,3$ (Kagawa et al, 1988, Takeuchi et al, 1988, Svensson et al., 1990). In other words, recombinant proteins expressed using the CHO system will differ from their natural counterparts in their type of terminal sialic acid linkages. This is another difference between natural and current recombinant products in addition to the lower overall sialic acid content of the latter, and is an important consideration in the production of biologicals for pharmaceutical use since the carbohydrate moieties may contribute to the pharmacological attributes of the molecule.

SUMMARY

It is therefore desirable to have a rhCG product that more closely replicates or mimics the physiochemical and pharmacokinetic profile of the product produced from human urine. It is desirable to have a rhCG product that has improved pharmacokinetic property or properties compared to the known recombinant product.

According to the present invention there is provided recombinant hCG ("rhCG" or "rechCG") including α2,3 sialylation and α2,6 sialylation and, optionally, α2,8 sialylation. The rhCG (or rhCG preparation) according to the invention may have a sialic acid content [expressed in terms of a ratio of moles of sialic acid to moles of protein] of 15 mol/mol or greater, for example of from 15 mol/mol to 25 mol/mol, for example from 17 mol/mol to 24 mol/mol, for example from 17.7 mol/mol to 23 mol/mol, for example from 18 mol/mol to 22 mol/mol, for example from 19 mol/mol to 21 mol/mol, for example from 19 mol/mol to 20 mol/mol. The rhCG (or rhCG preparation) according to the invention may have 10% or more of the total sialylation being α2,3-sialylation. For example, 45% to 80% of the total sialylation may be α2,3-sialylation, for example 50% to 70% of the total sialylation may be α2,3-sialylation, for example 55 to 65% of the total sialylation may be α2,3-sialylation. For example 65-85% of the total sialylation may be α2,3-sialylation. The rhCG (or rhCG preparation) of the invention may have 50% or less of the total sialylation being α2,6-sialylation. For example, 20-55% of the total sialylation may be α2,6-sialylation, for example, 30-50% of the total sialylation may be α2,6-sialylation, for example, 35-45% of the total sialylation may be α2,6-sialylation. For example 15-35% of the total sialylation may be α2,6-sialylation. The rhCG (or rhCG preparation) of the invention may have 5% or less of the total sialylation being α2,8-sialylation, for example 0 to 4%, e.g. 0.1-4% of the total sialylation may be α2,8-sialylation. The rhCG (or rhCG preparation) of the invention may have no α2,8-sialylation.

DESCRIPTION

Figure 1:
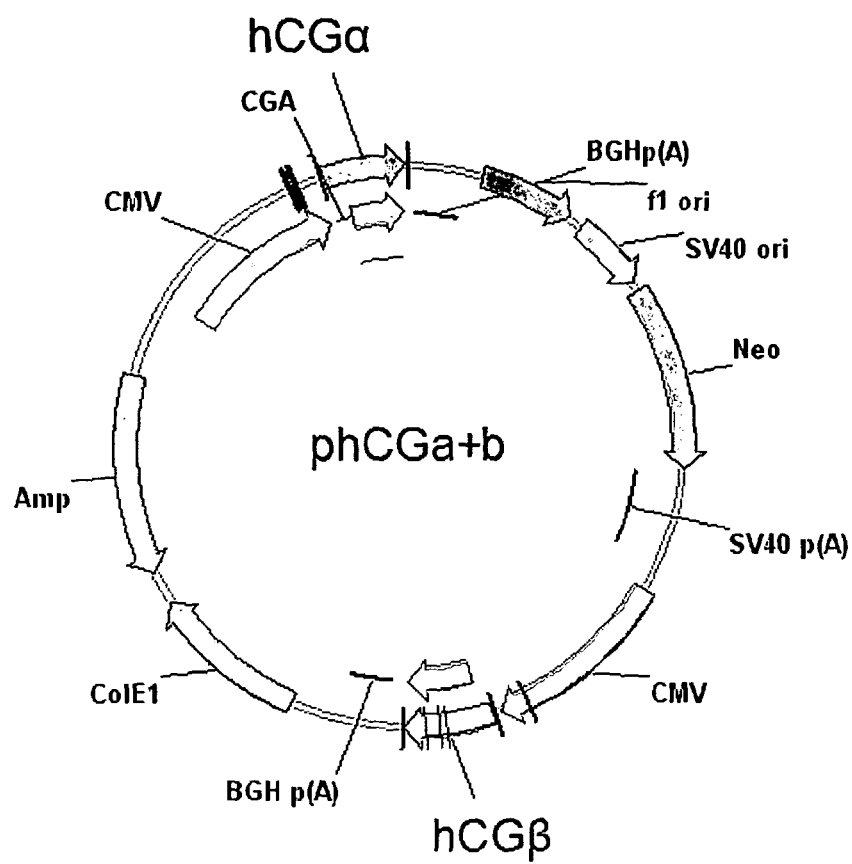
FIG. 1 is a plasmid map of the phCGalpha/beta expression vector.

The applicants have developed a human derived recombinant hCG which has a more acidic profile than the CHO derived product, OVITRELLE®, and which has a higher sialic acid content. The applicants' research indicates that the type of sialic acid linkage, α2,3- or α2,6-, can have a dramatic influence on biological clearance of hCG. Human cell lines, as opposed to CHO cell lines, can express recombinant hCG with sialic acids attached by both α2,3 and α2,6 linkages.

Recombinant hCG with a mixture of both α2,3 and α2,6-linked sialic acid was made by engineering a human cell line to express both rhCG and α2,3 sialyltransferase (Examples 4, 5a and 5b). The expressed product is highly acidic and carries a mix of both α2,3- and α2,6-linked sialic acids; the latter provided by the endogenous sialyl transferase activity. This has two advantages over rhCG expressed in conventional CHO cells: first the material is more highly sialylated due to the combined activities of the two sialyltransferases; and secondly the material more closely resembles the natural hCG. This is likely to be more biologically appropriate compared to CHO cell derived recombinant products that have produce only α2,3 linked sialic acid and have decreased sialic acid content.

The applicants have surprisingly found that rhCG of the invention may more closely replicate or mimic the physiochemical and pharmacokinetic profile of the natural human urinary product than other recombinant products. In other words, rhCG of the invention may be closer to the "natural" hCG. This may have significant advantages regarding dosing etc. Further, a more "natural" or more "human" product may be more desirable to the patient, who may desire therapy, although in a sense artificial, to be as "natural" as possible. There may be other advantages (e.g. pharmacokinetic advantages) in a recombinant hCG product having carbohydrate (e.g. glycan) structure which is closer to natural (e.g. human urinary) hCG than other recombinant products.

The invention is thus a recombinant version of hCG which carries a mix of α2,3 and α2,6 sialic acid and therefore more closely resembles natural hCG. It is expected that the use of this compound for controlled ovarian stimulation, in IVF techniques, and ovulation induction will result in a more natural stimulation of the ovary compared to existing recombinant products.

According to the present invention there is provided recombinant hCG ("rhCG" or "rechCG") (and/or a recombinant hCG preparation) including α2,3 sialylation and α2,6 sialylation. The rhCH or rhCG preparation may optionally further include α2, 8 sialylation.

Herein term "recombinant hCG preparation" includes a preparation for e.g. pharmaceutical use which includes recombinant hCG. In embodiments of the invention, the rhCG may be present as a single isoform or as a mixture of isoforms.

The rhCG (or rhCG preparation) according to the invention may have a sialic acid content [expressed in terms of a ratio of moles of sialic acid to moles of protein] of 15 mol/mol or greater (Example 8), for example of from 15 mol/mol to 25 mol/mol, for example from 17 mol/mol to 24 mol/mol, for example from 17.7 mol/mol to 23 mol/mol, for example from 18 mol/mol to 22 mol/mol, for example from 19 mol/mol to 21 mol/mol, for example from 19 mol/mol to 20 mol/mol. The rhCG of the invention may be produced or expressed in a human cell line.

The rhCG (or rhCG preparation) according to the invention may have 10% or more of the total sialylation being α2,3-sialylation. For example, 20, 30, 40, 45, 50, 55, 60, 70, 80 or 90% or more of the total sialylation may be α2,3-sialylation. The rhCG (or rhCG preparation) may include α2,3-sialylation in an amount which is from 45% to 80% of the total sialylation, for example 50% to 70% of the total sialylation, for example 55 to 65% of the total sialylation. The rhCG (or rhCG preparation) may include α2,3-sialylation in an amount which is from 65 to 85% of the total sialylation, for example from 70 to 80% of the total sialylation, for example from 71 to 79% of the total sialylation. The rhCG (or rhCG preparation) of the invention may have 50% or less of the total sialylation being α2,6-sialylation. For example 45, 40, 30, 20, 10, 5% or less of the total sialylation may be α2,6-sialylation. The rhCG (or rhCG preparation) may include α2,6-sialylation in an amount which is from 20-55% of the total sialylation, for example, 30-50% of the total sialylation, for example 35-45% of the total sialylation. The rhCG (or rhCG preparation) may include α2,6-sialylation in an amount which is from 15 to 35% of the total sialylation, for example from 20 to 30% of the total sialylation, for example from 21 to 29% of the total sialylation. The rhCG (or rhCG preparation) of the invention may have 5% or less of the total sialylation being α2,8-sialylation. For example 2.5% or less of the total sialylation may be α2,8-sialylation. The rhCG (or rhCG preparation) may include α2,8-sialylation in an amount which is from 0 to 4% of the total sialylation, for example 0.1 to 4% of the total sialylation, for example from 0.5 to 3% of the total sialylation, for example from 0.5 to 2.5% of the total sialylation. The rhCG (or rhCG preparation) of the invention may have no α2,8-sialylation. By sialylation it is meant the amount of sialic residues present on the hCG carbohydrate structures. α2,3-sialylation means sialylation at the 2,3 position (as is well known in the art) and α2,6 sialylation at the 2,6 position (also well known in the art). Thus "% of the total sialylation may be α2,3 sialylation" refers to the % of the total number of sialic acid residues present in the hCG which are sialylated in the 2,3 position. The term "% of the total sialylation being α2,6-sialylation" refers to the % of the total number of sialic acid residues present in the hCG which are sialylated in the 2,6 position.

The rhCG (or rhCG preparation) according to the invention may have a sialic acid content (amount of sialylation per hCG molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

Recombinant hCG expressed in Chinese hamster ovary (CHO) cells includes exclusively α2,3 sialylation.

The rhCG of the invention may be produced or expressed in a human cell line. This may simplify (and render more efficient) the production method because manipulation and control of e.g. the cell growth medium to retain sialylation may be less critical than with known processes. The method may also be more efficient because there is less basic rhCG produced than in production of known rhCG products; more acidic rhCG is produced and separation/removal of basic hCG is less problematic. The rhCG may be produced or expressed in a PER.C6® cell line, a Per.C6 derived cell line or a modified PER.C6® cell line. The cell line may be feed using α2,3-sialyltransferase. The rhCG may include α2,6-linked sialic acids (α2,6 sialylation) provided by endogenous sialyl transferase activity {of the cell line]. Alternatively or additionally, the cell line may be modified using α2,6-sialyltransferase.

The rhCG may be produced using α2,3-sialyltransferase. The rhCG may include α2,6-linked sialic acids (α2,6 sialylation) provided by endogenous sialyl transferase activity. The rhCG may be produced using α2,3- and/or α2,6-sialyltransferase.

According to the present invention in a further aspect there is provided a method of production of rhCG and/or an rhCG preparation as described herein (according to aspects of the invention) comprising the step of producing or expressing the rhCG in a human cell line, for example a PER.C6® cell line, a PER.C6® derived cell line or a modified PER.C6® cell line, for example a cell line which has been modified using α2,3-sialyltransferase.

The rhCG structure contains glycan moieties. Branching can occur with the result that the glycan may have 1, 2, 3, 4 or more terminal sugar residues or "antennae", as is well known in the art. The rhCG of the invention may have glycans with sialylation presence on mono-antennary and/or di-antennary and/or tri-antennary and/or tetra-antennary structures. The rhCG may include mono-sialylated, di-sialylated, tri-sialylated and tetra-sialylated glycan structures, for example with relative amounts as follows: 0.1-4% mono-sialylated; 35-45% di-sialylated; 0.5-8% tri-sialylated and 0-1% tetra-sialylated (e.g. as shown by WAX analysis of charged glycans, as set out in Example 8D). Preferably, the recombinant hCG of the invention includes mono (1S), di(2S), tri(3S) and tetra(4S) sialylated structures. Preferably, the relative amounts of sialylated structures are in the following ratios (1S:2S:4S:4S): 0.2-1%:35-40%:2.5-7%:0.5-1% (e.g. as shown by WAX analysis of charged glycans, as set out in Example 8D).

According to the present invention in a further aspect there is provided rhCG produced (e.g. expressed) in a human cell line. The rhCG may include α2,3- and α2,6-sialylation. The rhCG may be produced or expressed in a PER.C6® cell line, a PER.C6® derived cell line or a modified PER.C6® cell line. The cell line may be modified using α2,3-sialyltransferase. The rhCG may include α2,6-linked sialic acids (α2,6 sialylation) provided by endogenous sialyl transferase activity [of the cell line]. Alternatively or additionally, the cell line may be modified using α2,6-sialyltransferase. The rhCG (or rhCG preparation) according to the invention may have a sialic acid content [expressed in terms of a ratio of moles of sialic acid to moles of protein] of 15 mol/mol or greater, for example of from 15 mol/mol to 25 mol/mol, for example of from 17 mol/mol to 24 mol/mol, for example from 17.7 mol/mol to 23 mol/mol, for example from 18 mol/mol to 22 mol/mol, for example from 19 mol/mol to 21 mol/mol, for example from 19 mol/mol to 20 mol/mol. The rhCG (or rhCG preparation) may have 10% or more of the total sialylation being α2,3-sialylation, for example 45% to 80% of the total sialylation may be α2,3-sialylation, for example 50% to 70% of the total sialylation may be α2,3-sialylation, for example 55 to 65% of the total sialylation may be α2,3-sialylation. For example 65-85% of the total sialylation may be α2,3-sialylation. The rhCG (or rhCG preparation) of the invention may have 50% or less of the total sialylation being α2,6-sialylation. For example, 20-55% of the total sialylation may be α2,6-sialylation, for example, 30-50% of the total sialylation may be α2,6-sialylation, for example, 35-45% of the total sialylation may be α2,6-sialylation. For example 15-35% of the total sialylation may be α2,6-sialylation. The rhCG (or rhCG preparation) of the invention may have 5% or less of the total sialylation being α2,8-sialylation, for example 0 to 4%, e.g. 0.5-4% of the total sialylation may be α2,8-sialylation. The rhCG (or rhCG preparation) of the invention may have no α2,8-sialylation.

According to the present invention in a further aspect there is provided a pharmaceutical composition comprising rhCG including α2,3-sialylation and α2,6-sialylation (e.g. as set out above). The pharmaceutical composition may further comprise FSH and/or LH.

FSH can be obtained by any means known in the art. FSH as used herein includes human-derived and recombinant FSH. Human-derived FSH can be purified from any appropriate source (e.g. urine) by any method known in the art. The FSH may be recombinant FSH—for example expressed in a human cell line. Methods of expressing and purifying recombinant FSH are well known in the art.

LH can be obtained by any means known in the art. LH, as used herein, includes human-derived and recombinant LH. Human-derived LH can be purified from any appropriate source (e.g. urine) by any method known in the art. Methods of expressing and purifying recombinant LH are known in the art.

The pharmaceutical composition may be for the treatment of infertility, e.g. for use in e.g. assisted reproductive technologies (ART), ovulation induction or intrauterine insemination (IUD. The pharmaceutical composition may be used, for example, in medical indications where known hCG preparations are used. The present invention also provides the use of rhCG and/or an rhCG preparation described herein (according to aspects of the invention) for, or in the manufacture of a medicament for, the treatment of infertility. The pharmaceutical compositions of the present invention can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectible organic esters such as ethyl oleate.

The compositions of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of hCG (and other active ingredients, if present) from subcutaneous or intramuscular injection. This can be accomplished by the use of a liquid suspension of crystalline or amorphous material with poor water solubility. The rate of absorption of hCG then depends upon its rate of dissolution which, in turn, can depend upon crystal size and crystalline form. Alternatively, delayed absorption of a parenterally administered hCG combination form is accomplished by dissolving or suspending the hCG combination in an oil vehicle.

Injectable depot forms can be made by forming microencapsule matrices of the hCG (and other agents, if present) in biodegradable polymers such as polylactide-polyglycolide. Depending upon the ratio of hCG to polymer and the nature of the particular polymer employed, the rate of hCG release can be controlled. Examples of other biodegradable polymers include polyvinylpyrrolidone, poly(orthoesters), poly(anhydrides) etc. Depot injectable formulations are also prepared by entrapping the hCG in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

Injectable formulations can be supplied as a product having pharmaceutical compositions containing hCG (optionally with FSH, LH etc.) If there is more than one active ingredient (i.e. hCG and e.g. FSH or LH) these may be suitable for administration separately or together. If administered separately, administration can be sequential. The product can be supplied in any appropriate package. For example, a product can contain a number of pre-filled syringes containing either hCG, FSH, or a combination of both FSH and hCG, the syringes packaged in a blister package or other means to maintain sterility. A product can optionally contain instructions for using the hCG and FSH formulations.

The pH and exact concentration of the various components of the pharmaceutical composition are adjusted in accordance with routine practice in this field. See GOODMAN and GILMAN's THE PHARMACOLOGICAL BASIS FOR THERAPEUTICES, $7^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

The present invention will now be described in more detail with reference to the following Examples and to the attached drawings.

Sequence Selection

Human hCG

The coding region of the gene for the hCG alpha polypeptide was used according to Fiddes and Goodman (1979). The sequence is banked as AH007338 and at the time of construction there were no other variants of this protein sequence. The nucleic acid sequence is referred to herein as SEQ ID NO:1 and the polypeptide sequence is referred to as SEQ ID NO:5.

The coding region of the gene for hCG beta polypeptide was used according to Fiddes and Goodman (1980). The sequence is banked as NP_000728 and is consistent with the protein sequences of CGbeta3, CGbeta5 and CGbeta7. The nucleic acid sequence is referred herein as SEQ ID NO:2 and the polypeptide sequence is referred to as SEQ ID NO:6.

Sialyltransferase

α2,3-Sialyltransferase—The coding region of the gene for beta-galactoside alpha-2,3-sialyltransferase 4 (α2,3-sialyltransferase, ST3GAL4) was used according to Kitagawa and Paulson (1994). The sequence is banked as L23767. The nucleic acid sequence is referred to herein as SEQ ID NO:3 and the polypeptide sequence is referred to as SEQ ID NO:7.

α2,6-Sialyltransferase—The coding region of the gene for beta-galactosamide alpha-2,6-sialyltransferase 1 (α2,6-sialyltransferase, ST6GAL1) was used according to Grundmann et al. (1990). The sequence is banked as NM_003032. The nucleic acid sequence is and referred to herein as SEQ ID NO: 4 and the polypeptide sequence is referred to as SEQ ID NO:8.

EXAMPLES

Example 1

Construction of the hCG Expression Vector

The coding sequence of hCG alpha polypeptide (AH007338, SEQ ID NO:1) and hCG beta polypeptide (NP_000728, SEQ ID NO:2) were amplified by PCR using the primer combinations CGa-fw and CGa-rev and CGb-fw and CGb-rec respectively.

```
CGa-fw                                  (SEQ ID NO: 9)
5'-CCAGGATCCGCCACCATGGATTACTACAGAAAAATATGC-3';

CGa-rev                                 (SEQ ID NO: 10)
5'-GGATGGCTAGCTTAAGATTTGTGATAATAAC-3';

CGb-fw                                  (SEQ ID NO: 11)
5'-CCAGGCGCGCCACCATGGAGATGTTCCAGGGGCTGC-3';
and CGb-rev                                 (SEQ ID NO: 12)
5'-CCGGGTTAACTTATTGTGGGAGGATCGGGG-3'.
```

The resulting amplified hCG beta DNA was digested with the restriction enzymes AscI and HpaI and inserted into the AscI and HpaI sites on the CMV driven mammalian expression vector carrying a neomycin selection marker. Similarly the hCG alpha DNA was digested with BamHI and NheI and inserted into the sites BamHI and NheI on the expression vector already containing the hCG beta polypeptide DNA.

The vector DNA was used to transform the DH5α strain of E. coli. Colonies were picked for amplification and, of the number which included the vector containing both hCG alpha and beta, twenty were selected for sequencing. All colonies selected for sequencing contained the correct sequences according to SEQ ID NO:1 and SEQ ID NO:2. Plasmid phCG A+B was selected for transfection (FIG. 1).

Example 2

Construction of the ST3 Expression Vector

The coding sequence of beta-galactoside alpha-2,3-sialyltransferase 4 (ST3, L23767, SEQ ID NO:3) was amplified by PCR using the primer combination 2,3STfw and 2,3STrev.

```
2,3STfw                                 (SEQ ID NO: 13)
5'-CCAGGATCCGCCACCATGTGTCCTGCAGGCTGGAAGC-3';
and 2,3STrev                                (SEQ ID NO: 14)
5'-TTTTTTTCTTAAGTCAGAAGGACGTGAGGTTCTTG-3'.
```

Figure 2:
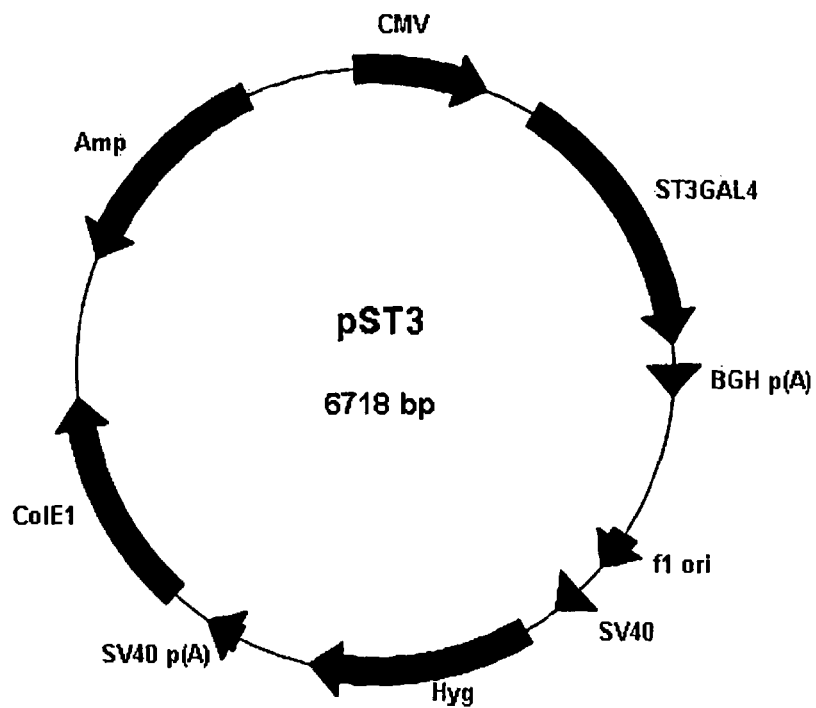
FIG. 2 is a representation of the α2,3-sialyltransferase (ST3GAL4) expression vector.

The resulting amplified ST3 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST3#1 (FIG. 2) contained the correct sequence according to SEQ ID NO:3 and was selected for transfection.

Example 3

Construction of the ST6 Expression Vector

The coding sequence of beta-galactosamide alpha-2,6-sialyltransferase 1 (ST6, NM 003032, SEQ ID NO:4) was amplified by PCR using the primer combination 2,6STfw and 2,6STrev.

```
2,6STfw                                 (SEQ ID NO: 15)
5'-CCAGGATCCGCCACCATGATTCACACCAACCTGAAG-3';
and 2,6STrev                                (SEQ ID NO: 16)
5'-TTTTTTTCTTAAGTTAGCAGTGAATGGTCCGG-3'.
```

Figure 3:
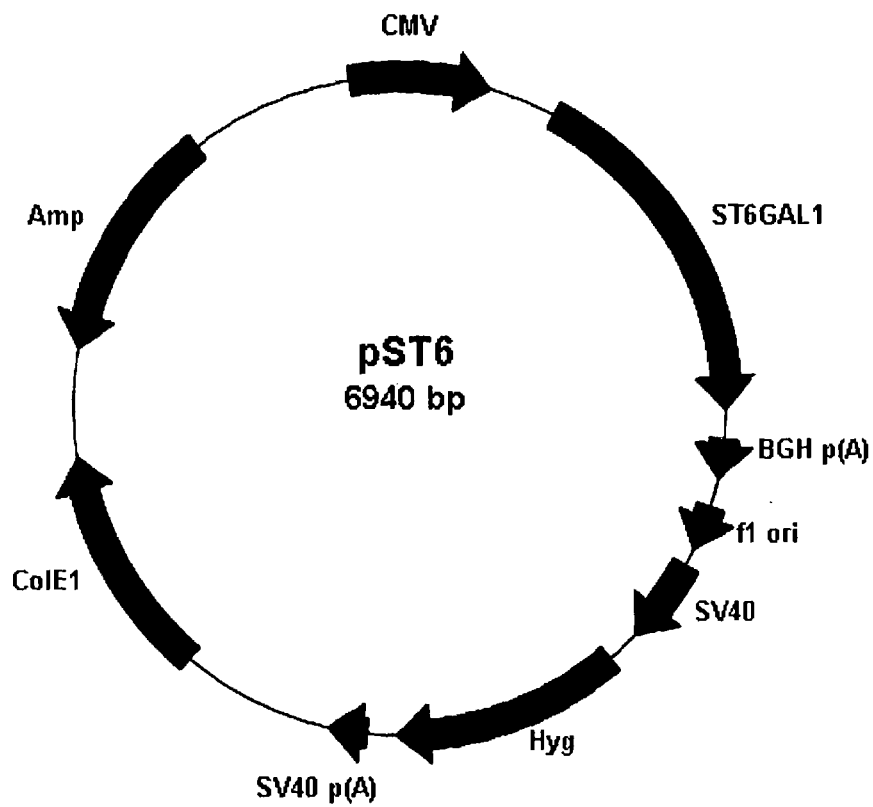
FIG. 3 is a representation of the α2,6-sialyltransferase (ST6GAL1) expression vector.

The resulting amplified ST6 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST6#11 (FIG. 3) contained the correct sequence according to SEQ ID NO:4 and was selected for transfection.

Example 4

Stable Expression of phCG A+B in PER.C6® Cells. Transfection Isolation and Screening of Clones PER.C6® Clones producing hCG were generated by expressing both polypeptide chains of hCG from a single plasmid (see Example 1).

To obtain stable clones a liposome based transfection agent was used with the phCG A+B construct. Stable clones were selected in PER.C6® selection media supplemented with 10% FCS and containing G418. Three weeks after transfection G418 resistant clones grew out. A total of 389 clones were selected for isolation. The isolated clones were cultured in selection medium until 70-80% confluent. Supernatants were assayed for hCG protein content using an hCG selective ELISA and pharmacological activity at the hCG receptor in cloned cell line, using a cAMP accumulation assay. Clones (118) expressing functional protein were progressed for culture expansion to 24 well, 6 well and T80 flasks.

Studies to determine productivity and quality of the material from 47 clones were initiated in T80 flasks to generate sufficient material. Cells were cultured in supplemented media as previously described for 7 days and the supernatant harvested. Productivity was determined using the hCG selective ELISA. The isoelectric profile of the material was determined (using the method described in Example 6). The information from the IEF was used to select clones for metabolic clearance rate analysis. Clones with sufficient productivity and quality were selected for sialyltransferase engineering.

Example 5a

Level of Sialylation is Increased in Cells that Over Express α2,3-Sialyltransferase. Stable Expression of pST3 in hCG Expressing PER.C6® Cells; Transfection Isolation and Screening of Clones PER.C6® clones producing highly sialylated hCG were generated by expressing α2,3 sialyltransferase from separate plasmids (see Example 2) in PER.C6® cells already expressing both polypeptide chains of hCG (see Example 4). Clones produced from PER.C6® cells as set out in Example 4 were selected for their characteristics including productivity, good growth profile, production of functional protein, and produced hCG which included some sialylation.

Stable clones were generated as previously described in Example 4. Clones from the α2,3-sialyltransferase program were isolated, expanded and assayed. The final clone number for the α2,3-study was five. The α2,3-sialyltransferase clones were adapted to serum free media and suspension conditions.

As before, clones were assayed using a hCG selective ELISA, functional response in an hCG receptor cell line, IEF (Example 6). They were also assessed for metabolic clearance rate (Example 9) and USP hCG Bioassay (Example 10). Results were compared to a commercially available recombinant hCG (OVITRELLE®, Serono) and the parental hCG PER.C6® cell lines. Representative samples are shown in the Examples and Figures.

In conclusion, expression of hCG together with α2,3-sialyltransferase in PER.C6® cells results in increased levels of sialylated hCG compared to cells expressing hCG only.

Example 5b

Stable Expression of pST3 in hCG Expressing PER.C6® Cells—a Different Method

The alpha beta heterodimer produced above (Example 4) had a low level of sialylation resulting in a very basic IEF profile. As indicated above (Example 5a) expression of hCG together with α2,3-sialyltransferase in PER.C6® cells results in increased levels of sialylated hCG compared to cells expressing hCG only.

A double transfection of the hCG alpha and beta subunit genes together with the α2,3 sialyltransferase enzyme gene into PER.C6® cells in suspension cell culture format was performed. Cell lines were generated by co-transfecting the hCG vector (dual alpha/beta, Example 1) and the vector encoding α2,3-sialyltransferase (Example 2) under serum free conditions. Clones produced from PER.C6® cells were selected for their characteristics including productivity, good growth profile, production of functional protein, and produced hCG which included some sialylation. Clones were isolated, expanded and assayed.

As before, clones were assayed using a hCG selective ELISA, functional response in an hCG receptor cell line, IEF (Example 6). They were also assessed for metabolic clearance rate (Example 9) and USP hCG Bioassay (Example 10). Results were compared to a commercially available recombinant hCG (OVITRELLE®, Serono) and the parental hCG PER.C6® cell lines. Representative samples are shown in the Examples and Figures (see Examples 6, 9, 10, FIGS. 4 and 5). The recombinant hCG produced by the clones (that is, recombinant hCG according to the invention) has significantly improved sialylation (i.e. on average more hCG isoforms with high numbers of sialic acids), compared to hCG expressed without α2,3-sialyltransferase and OVITRELLE® (see Examples 6 and 8, FIG. 4).

Example 6

Analysis of the Isoelectric Point pI of PER.C6® Cell Produced hCG Isoforms by Isoelectric Focussing Electrophoresis is defined as the transport of charged molecules through a solvent by an electrical field. The mobility of a biological molecule through an electric field will depend on the field strength, net charge on the molecule, size and shape of the molecule, ionic strength and properties of the medium through which the molecules migrate.

Isoelectric focusing (IEF) is an electrophoretic technique for the separation of proteins based on their pI. The pI is the pH at which a protein has no net charge and will not migrate in an electric field. The sialic acid content of the hCG isoforms subtly alters the pI point for each isoform, which can be exploited using this technique to visualise the PER.C6® cell produced hCG isoforms from each clone.

The isoelectric points of the PER.C6® cell produced hCG isoforms in cell culture supernatants were analyzed using isoelectric focussing. Cell culture media from PER.C6® cell produced hCG clones were produced as described in Example 4, 5a and 5b.

PER.C6® cell produced hCG samples were separated on NOVEX® IEF Gels containing 5% polyacrylamide under native conditions on a pH 3.0-7.0 gradient in an ampholyte solution pH 3.0-7.0. Protein's were visualised using Coomassie Blue staining, using methods well known in the art.

Figure 4:
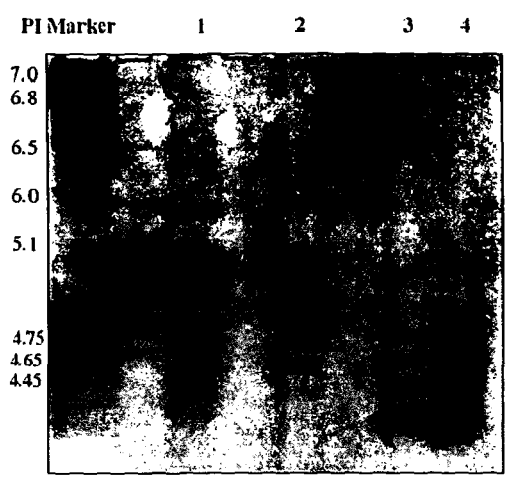
FIG. 4 is a representation of an isoelectric focusing gel, with Coomassie Blue staining, comparing rhCG Isoforms in human cell line derived recombinant hCG preparations according to the invention (track 3, 4) with preparations of the prior art (track 1, 2).

FIG. 4 shows the detection of rhCG Isoforms by IEF stained with Coomassie Blue in compositions according to the invention (Track 3, 10 μg, and Track 4, 15 μg) and the CHO derived composition of the prior art, OVITRELLE® (Track 1, OVITRELLE®, 10 μg, and Track 2, OVITRELLE®, 15 μg). The bands represent isoforms of hCG containing different numbers of sialic acid molecules. Using this method clones producing hCG isoforms with a higher number of sialic acid molecules were identified. FIG. 4 indicates that human cell line derived recombinant hCGs engineered with α2,3-sialyltransferase (compositions according to the invention) have a more acidic profile than OVITRELLE®.

Example 7

Analysis of the Sialic Acid Linkages of PER.C6® Cell Produced hCG

Glycoconjugates were analyzed using a lectin based glycan differentiation method. With this method glycoproteins and glycoconjuagtes bound to nitrocellulose can be characterized. Lectins selectively recognize a particular moiety, for example α2,3 linked sialic acid. The lectins applied are conjugated with the steroid hapten digoxigenin which enables immunological detection of the bound lectins.

Purified PER.C6® cell produced hCG from a parental clone (no additional sialyltransferase), and a α2,3-sialyltransferase engineered clone were separated using standard SDS-PAGE techniques. A commercially available recombinant hCG (OVITRELLE®, Serono) was used as a standard.

Sialic acid was analyzed using the DIG Glycan Differentiation Kit (Cat. No. 11 210 238 001, Roche) according to the manufacturers instructions. Positive reactions with *Sambucus nigra* agglutinin (SNA) indicated terminally linked (2-6) sialic acid. Positive reactions with Maackia amurensis agglutinin II (MAA): indicated terminally linked (α2-3) sialic acid In summary the parental clone contained low levels of both α2,3- and α2,6-sialic acid. The clones engineered with α2,3-sialyltransferase contained high levels of α2,3-sialic acid linkages and low levels of α2,6-sialic acid linkages. The standard control OVITRELLE® only contains α2,3-sialic acid linkages. This is consistent with what is known about recombinant proteins produced in Chinese Hamster ovary (CHO) cells (Kagawa et al., 1988, Takeuchi et al., 1988, Svensson et al., 1990).

In conclusion, engineering of PER.C6® hCG cells with α2,3-sialyltransferase successfully increased the number of sialic acid molecules conjugated to the recombinant hCG in the sample.

Examples 8A and 8B

Quantification of Total Sialic Acid

Sialic acid is a protein-bound carbohydrate considered to be a mono-saccharide and occurs in combination with other mono-saccharides like galactose, mannose, glucosamine, galactosamine and fucose. The total sialic acid on purified rhCG according to the invention was measured using a method based on the method of Stanton et. al. (J. Biochem. Biophys. Methods. 30 (1995), 37-48).

Example 8A

The total sialic acid content of PER.C6® cell produced recombinant hCG modified with α2,3-sialyltransferase (e.g. Example 5a, Example 5b) was measured and found to be greater than 15 mol/mol, [expressed in terms of a ratio of moles of sialic acid to moles of protein], for example greater than 18 mol/mol, for example 19.1 mol/mol. This can be compared to OVITRELLE®, which has total sialic acid content of 17.6 mol/mol.

Example 8B

The total sialic acid content of PER.C6® cell produced recombinant hCG modified with α2,3-sialyltransferase 080019-19 (prepared by the methods of Example 5b above) was measured and found to be 20 mol/mol, [expressed in terms of a ratio of moles of sialic acid to moles of protein]. Again, this may be favourably compared with OVITRELLE®, which has total sialic acid content of 17.6 mol/mol. This Example (080019-19) was tested to quantify the relative amounts of α2,3 and α2,6 sialic acid (Example 8C).

Example 8C

Quantification of Relative Amounts of α2,3 and α2,6 Sialic Acid

The relative percentage amounts of α2,3 and α2,6 sialic acid on purified rhCG [Example (080019-19), and two other Examples prepared by the methods of Example 5] were measured using known techniques—HPLC with Normal-phase (NP).

To quantify the alpha 2,3 and 2,6 sialic acid in O-link glycans the following analysis was performed. The O-linked glycans were cleaved from the hCG sample using an Orela Glycan Release Kit and separated on NP-HPLC. Samples of the extracted, pooled, glycans (extracted as above) were digested with different sialidases to determine the linkages. This Enzymatic degradation of glycans was performed using alpha 2-3,6,8 sialidase and alpha 2-3, sialidase. The enzymatic digested glycans were then re-separated on the NP column, and the O-Glycans were identified on the NP-HPLC using prepared standards. The relative percentages were calculated and are shown in the following table (SA=Sialic Acid).

| | % SA | | |
|---|---|---|---|
| Structure | 080019-19 | 09PD-84-04 | 09PD84-006-3 |
| α 2,3 SA | 59 | 63 | 63 |
| α 2,6 SA | 41 | 37 | 37 |

The relative percentages were found to be in the ranges 55%-65% (e.g. 59%) for α2,3 sialylation; and 35 to 45% (e.g. 41%) for α2,6 sialylation.

Example 8D

Quantification of Relative Amounts Mono, Di, Tri and Tetra Antennary Sialylated Structures The relative percentage amounts of mono, di, tri and tetra sialylated structures on glycans extracted from purified rhCG (the three samples used in Example 8C) were measured using known techniques.

Each sample of rhCG was immobilized (gel block), washed, reduced, alkylated and digested with PNGase F overnight. The N-glycans were then extracted and processed. N-glycans for NP-HPLC and WAX-HPLC analysis were labelled with the fluorophore 2AB as detailed in Royle et al.

Weak anion exchange (WAX) HPLC to separate the N-glycans by charge (Example 8C) was carried out as set out in Royle et al, with a Fetuin N-glycan standard as reference. Glycans were eluted according to the number of sialic acids they contained. All samples included mono (1S), di(2S), tri (3S) and tetra(4S) sialylated structures. The relative amounts of sialylated structures were found to be in the following ratios (1S:2S:4S:4S): 0.1-4%:35-45%:0.5-8%:0-1%.

A preferred example, 080019-19, included mono (13), di(2S), tri(3S) and tetra(4S) sialylated structures. The relative amounts of sialylated structures were in the following ratios (1S:2S:4S:4S): 0.1-4%:35-45%:0.5-8%:0-1%.

Example 9

Determination of the Metabolic Clearance Rates of rhCG

Figure 5:
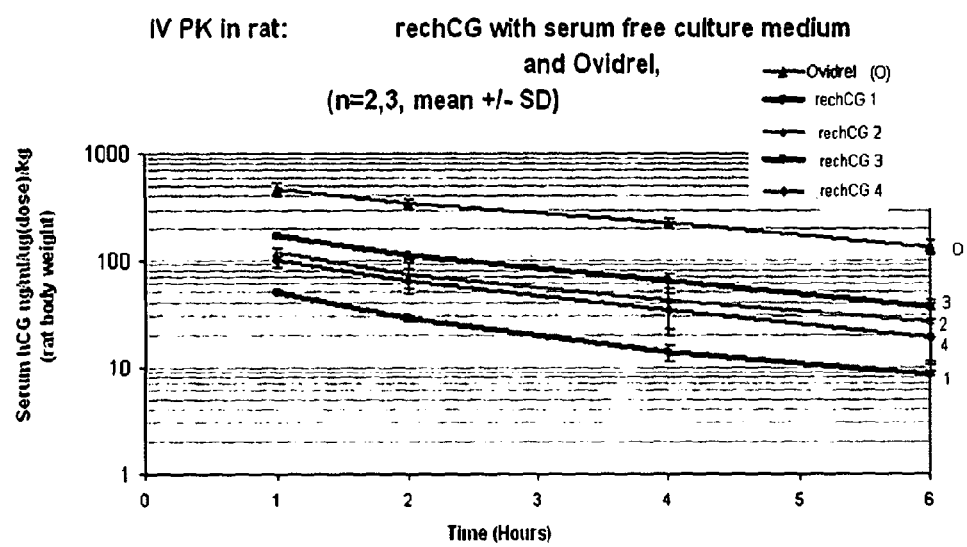
FIG. 5 is a graph that shows metabolic clearance rates (MCRs) of α2,3-sialytransferase engineered PER.C6® cell produced hCG samples.
Figure 6:
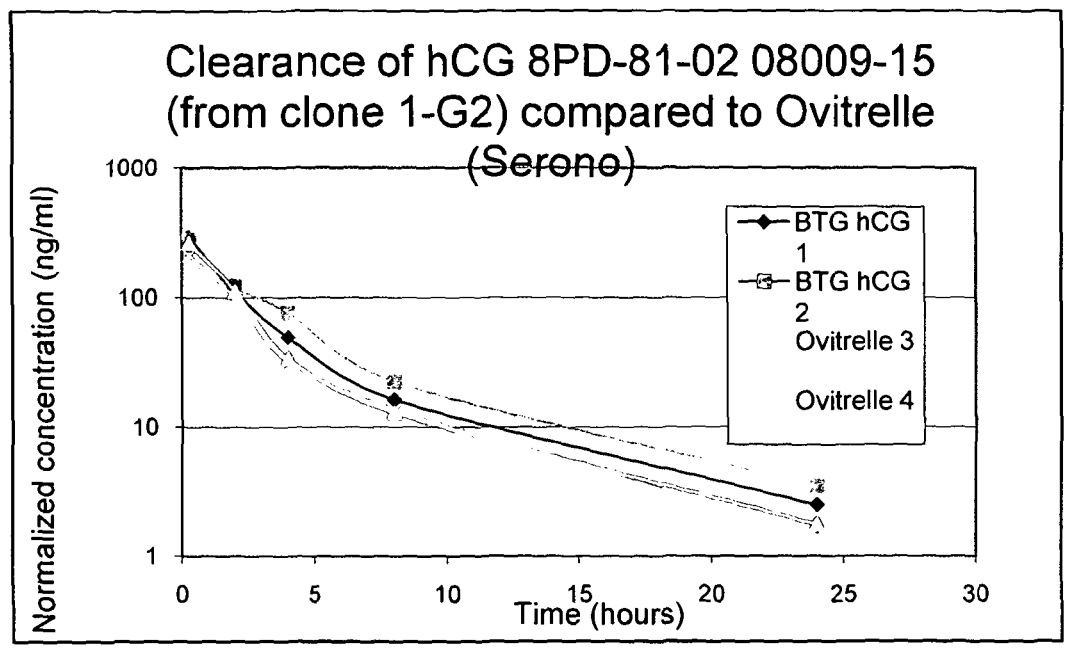
FIG. 6 is a graph that shows long term MCRs of α2,3 sialyltransferase engineered PER.C6® cell prepared rhCG samples

To determine the metabolic clearance rate (MCR) of PER.C6® cell produced hCG samples engineered using α2,3-sialyltransferase (e.g. Example 5a, 5b), conscious female rats (3 animals per clone) were injected into the tail vein at time zero with a bolus of rhCG (1-10 μg/rat, based on ELISA quantification of samples, DRG EIA 1288). Blood samples (400 μl) were taken from the tip of the tail at 1, 2, 4, 8, 12, 24 and 32 hours after test sample injection. Serum was collected by centrifugation and assayed for hCG content by ELISA (DRG EIA 1288). The MCR of PER.C6® cell produced hCG samples engineered using α2,3-sialyltransferase showed that the half life was similar to the standard (FIG. 5). FIG. 6 shows that other hCG samples engineered using α2,3-sialyltransferase may have improved half life compared to the standard (FIG. 6).

Example 10 hCG Bioassay According to USP

A hCG Bioassay was carried out, to assay the hCG specific activity. The activity was measured according to USP (USP Monographs: Chorionic Gonadotropin, USPC Official Aug. 1, 2009-Nov. 30, 2009), using OVITRELLE® as a standard. OVITRELLE® has a biological activity of 26,000 IU/mg (Curr. Med. Res. Opin. 2005 December; 21(12): 1969-76). The acceptance limit was >21,000 IU hCG/mg. The biological activity for a sample of human cell line derived hCG recombinant hCG engineered with α2,3-sialyltransferase (having sialic acid content 19.1 mol/mol—see Example 8) was 27,477 IU hCG/mg.

Example 11

Production and Purification Overview

A procedure was developed to produce recombinant hCG in PER.C6® cells that were cultured in suspension in serum free medium. The procedure is described below and was applied to several hCG-producing PER.C6® cell lines.

Recombinant hCG from an α2,3-clone was prepared using a using a modification of the method described by Lowry et al. (1976).

For the production of PER.C6® cell-produced hCG, the cell lines were adapted to a serum-free medium, i.e., EX-CELL® 525 (JRH Biosciences). The cells were first cultured to form a 70%-90% confluent monolayer in a T80 culture flask. On passage the cells were re-suspended in the serum free medium, EX-CELL® 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $>1 \times 10^6$ cells/ml, the cells were sub-cultured to a cell density of 0.2 or $0.3 \times 10^6$ cells/ml and further cultured in shaker flasks at 37° C., 5% $CO_2$ and 100 rpm.

For the production of hCG, the cells were transferred to a serum-free production medium, i.e., VPRO (JRH Biosciences), which supports the growth of PER.C6® cells to very high cell densities (usually $>10^7$ cells/ml in a batch culture). The cells were first cultured to $>1 \times 10^6$ cells/ml in EX-CELL® 525, then spun down for 5 min at 1000 rpm and subsequently suspended in VPRO medium+6 mM L-glutamine to a density of $1 \times 10^6$ cells/ml. The cells were then cultured in a shaker flask for 7-10 days at 37° C., 5% $CO_2$ and 100 rpm. During this period, the cells grew to a density of $>10^7$ cells/ml. The culture medium was harvested after the cell viability started to decline. The cells were spun down for 5 min at 1000 rpm and the supernatant was used for the quantification and purification of hCG. The concentration of hCG was determined using ELISA (DRG EIA 1288).

Thereafter, purification of hCG was carried out using a modification of the method described by Lowry et al. (1976). This was achieved by chromatography on DEAE cellulose, gel filtration on SEPHADEX® G100, adsorption chromatography on hydroxyapatite, and preparative polyacrylamide electrophoresis.

During all chromatographic procedures, the presence of immunoreactive recombinant hCG was confirmed by RIA (DRG EIA 1288) and IEF (Example 6).

REFERENCES

Andersen C Y, Westergaard L G, and van Wely M. (2004). FSH isoform composition of commercial gonadotrophin preparations: a neglected aspect? Reprod Biomed Online. 9(2), 231-236.

Bassett R M, and Driebergen R. (2005). Continued improvements in the quality and consistency of follitropin alfa, recombinant human FSH. Reprod Biomed Online. 10(2), 169-177.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Fiddes, J. C. and Goodman, H. M. (1979) Isolation, cloning and sequence analysis of the cDNA for the alpha-subunit of human chorionic gonadotropin. Nature, 281, 351-356.

Fiddes, J. C. and Goodman, H. M. (1980) The cDNA for the beta-subunit of human chorionic gonadotropin suggests evolution of a gene by readthrough into the 3'-untranslated region. Nature, 286, 684-387.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Lowry O H, Rosebrough N J, Farr A L, Randall R J. (1951) Protein measurement with the Folin phenol reagent. J Biol. Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Royle L, Radcliffe C M, Dwek R A and Rudd P M (2006) Methods in Molecular Biology, ed I Brockhausen-Schutzbach (Humana Press), 347: Glycobiology protocols, 125-144.

Steelman S L, and Pohley F M. (1953) Assay of the follicle stimulating hormone based on the augmentation with human chorionic gonadotropin. Endocrinology. 53(61, 604-616.

Svensson E C, Soreghan B, and Paulson J C. (1990) Organization of the beta-galactoside alpha 2,6-sialyltransferase gene. Evidence for the transcriptional regulation of terminal glycosylation. J Biol. Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol. Chem. 263(8), 3657-3663.

Ulloa-Aguirre A, Midgley A R Jr, Beitins I Z, and Padmanabhan V. (1995). Follicle-stimulating isohormones: characterization and physiological relevance. Endocr Rev. 16(6), 765-787.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

```
Human chorionic gonadotropin alpha polypeptide
Accession number AH007338
Nucleotide sequence of hCG alpha
   1 ATGGATTACT ACAGAAAATA TGCAGCTATC TTTCTGGTCA

CATTGTCGGT GTTTCTGCAT

61 GTTCTCCATT CCGCTCCTGA TGTGCAGGAT TGCCCAGAAT

GCACGCTACA GGAAAACCCA

121 TTCTTCTCCC AGCCGGGTGC CCCAATACTT CAGTGCATGG

GCTGCTGCTT CTCTAGAGCA

181 TATCCCACTC CACTAAGGTC CAAGAAGACG ATGTTGGTCC

AAAAGAACGT CACCTCAGAG

241 TCCACTTGCT GTGTAGCTAA ATCATATAAC AGGGTCACAG

TAATGGGGGG TTTCAAAGTG

301 GAGAACCACA CGGCGTGCCA CTGCAGTACT TGTTATTATC

ACAAATCTTA A (SEQ ID NO: 1)

Protein sequence of hCG alpha
   1 MKTLQFFFLF CCWKAICCNS CELTNITIAI EKEECRFCIS

INTTWCAGYC YTRDLVYKDP

61 ARPKIQKTCT FKELVYETVR VPGCAHHADS LYTYPVATQC

HCGKCDSDST DCTVRGLGPS

121 YCSFGEMKE (SEQ ID NO: 5)
```

-continued

Human Chorionic Gonadotrophin beta polypeptide
Accession number NP_000728
Nucleotide sequence of hCG beta
Nucleotide sequence
```
  1 ATGGAGATGT TCCAGGGGCT GCTGCTGTTG CTGCTGCTGA
GCATGGGCGG GACATGGGCA
 61 TCCAAGGAGC CGCTTCGGCC ACGGTGCCGC CCCATCAATG
CCACCCTGGC TGTGGAGAAG
121 GAGGGCTGCC CCGTGTGCAT CACCGTCAAC ACCACCATCT
GTGCCGGCTA CTGCCCCACC
181 ATGACCCGCG TGCTGCAGGG GGTCCTGCCG GCCCTGCCTC
AGGTGGTGTG CAACTACCGC
241 GATGTGCGCT TCGAGTCCAT CCGGCTCCCT GGCTGCCCGC
GCGGCGTGAA CCCCGTGGTC
301 TCCTACGCCG TGGCTCTCAG CTGTCAATGT GCACTCTGCC
GCCGCAGCAC CACTGACTGC
361 GGGGGTCCCA AGGACCACCC CTTGACCTGT GATGACCCCC
GCTTCCAGGA CTCCTCTTCC
421 TCAAAGGCCC CTCCCCCCAG CCTTCCAAGT CCATCCCGAC
TCCCGGGGCC CTCGGACACC
481 CCGATCCTCC CACAATAA (SEQ ID NO: 2)
```
Protein sequence of hCG beta
```
  1 MEMFQGLLLL LLLSMGGTWA SKEPLRPRCR PINATLAVEK
EGCPVCITVN TTICAGYCPT
 61 MTRVLQGVLP ALPQVVCNYR DVRFESIRLP GCPRGVNPVV
SYAVALSCQC ALCRRSTTDC
121 GGPKDHPLTC DDPRFQDSSS SKAPPPSLPS PSRLPGPSDT
PILPQ (SEQ ID NO: 6)
```

Beta-galactoside alpha-2,3-sialyltransferase 4
Accession Number L23767
Nucleotide sequence of ST3GAL4
```
  1 ATGTGTCCTG CAGGCTGGAA GCTCCTGGCC ATGTTGGCTC
TGGTCCTGGT CGTCATGGTG
 61 TGGTATTCCA TCTCCCGGGA AGACAGGTAC ATCGAGCTTT
TTTATTTTCC CATCCCAGAG
121 AAGAAGGAGC CGTGCCTCCA GGGTGAGGCA GAGAGCAAGG
CCTCTAAGCT CTTTGGCAAC
181 TACTCCCGGG ATCAGCCCAT CTTCCTGCGG CTTGAGGATT
ATTTCTGGGT CAAGACGCCA
241 TCTGCTTACG AGCTGCCCTA TGGGACCAAG GGGAGTGAGG
ATCTGCTCCT CCGGGTGCTA
301 GCCATCACCA GCTCCTCCAT CCCCAAGAAC ATCCAGAGCC
TCAGGTGCCG CCGCTGTGTG
361 GTCGTGGGGA ACGGGCACCG GCTGCGGAAC AGCTCACTGG
GAGATGCCAT CAACAAGTAC
421 GATGTGGTCA TCAGATTGAA CAATGCCCCA GTGGCTGGCT
ATGAGGGTGA CGTGGGCTCC
481 AAGACCACCA TGCGTCTCTT CTACCCTGAA TCTGCCCACT
TCGACCCCAA AGTAGAAAAC
541 AACCCAGACA CACTCCTCGT CCTGGTAGCT TTCAAGGCAA
TGGACTTCCA CTGGATTGAG
601 ACCATCCTGA GTGATAAGAA GCGGGTGCGA AAGGGTTTCT
GGAAACAGCC TCCCCTCATC
661 TGGGATGTCA ATCCTAAACA GATTCGGATT CTCAACCCCT
TCTTCATGGA GATTGCAGCT
721 GACAAACTGC TGAGCCTGCC AATGCAACAG CCACGGAAGA
TTAAGCAGAA GCCCACCACG
781 GGCCTGTTGG CCATCACGCT GGCCCTCCAC CTCTGTGACT
TGGTGCACAT TGCCGGCTTT
841 GGCTACCCAG ACGCCTACAA CAAGAAGCAG ACCATTCACT
ACTATGAGCA GATCACGCTC
901 AAGTCCATGG CGGGGTCAGG CCATAATGTC TCCCAAGAGG
CCCTGGCCAT TAAGCGGATG
961 CTGGAGATGG GAGCTATCAA GAACCTCACG TCCTTCTGA
(SEQ ID NO: 3)
```
Protein Sequence of ST3GAL4
```
  1 MCPAGWKLLA MLALVLVVMV WYSISREDRY IELFYFPIPE
KKEPCLQGEA ESKASKLFGN
 61 YSRDQPIFLR LEDYFWVKTP SAYELPYGTK GSEDLLLRVL
AITSSSIPKN IQSLRCRRCV
121 VVGNGHRLRN SSLGDAINKY DVVIRLNNAP VAGYEGDVGS
KTTMRLFYPE SAHFDPKVEN
181 NPDTLLVLVA FKAMDFHWIE TILSDKKRVR KGFWKQPPLI
WDVNPKQIRI LNPFFMEIAA
241 DKLLSLPMQQ PRKIKQKPTT GLLAITLALH LCDLVHIAGF
GYPDAYNKKQ TIHYYEQITL
301 KSMAGSGHNV SQEALAIKRM LEMGAIKNLT SF
(SEQ ID NO: 7)
```

Beta-galactosamide alpha-2,6-sialyltransferase 1
Accession number NM_003032
Nucleotide sequence of ST6GAL1
```
  1 ATGATTCACA CCAACCTGAA GAAAAAGTTC AGCTGCTGCG
TCCTGGTCTT TCTTCTGTTT
 61 GCAGTCATCT GTGTGTGGAA GGAAAAGAAG AAAGGGAGTT
ACTATGATTC CTTTAAATTG
121 CAAACCAAGG AATTCCAGGT GTTAAAGAGT CTGGGGAAAT
TGGCCATGGG GTCTGATTCC
```

181 CAGTCTGTAT CCTCAAGCAG CACCCAGGAC CCCCACAGGG GCCGCCAGAC CCTCGGCAGT

241 CTCAGAGGCC TAGCCAAGGC CAAACCAGAG GCCTCCTTCC AGGTGTGGAA CAAGGACAGC

301 TCTTCCAAAA ACCTTATCCC TAGGCTGCAA AAGATCTGGA AGAATTACCT AAGCATGAAC

361 AAGTACAAAG TGTCCTACAA GGGGCCAGGA CCAGGCATCA AGTTCAGTGC AGAGGCCCTG

421 CGCTGCCACC TCCGGGACCA TGTGAATGTA TCCATGGTAG AGGTCACAGA TTTTCCCTTC

481 AATACCTCTG AATGGGAGGG TTATCTGCCC AAGGAGAGCA TTAGGACCAA GGCTGGGCCT

541 TGGGGCAGGT GTGCTGTTGT GTCGTCAGCG GGATCTCTGA AGTCCTCCCA ACTAGGCAGA

601 GAAATCGATG ATCATGACGC AGTCCTGAGG TTTAATGGGG CACCCACAGC CAACTTCCAA

661 CAAGATGTGG GCACAAAAAC TACCATTCGC CTGATGAACT CTCAGTTGGT TACCACAGAG

721 AAGCGCTTCC TCAAAGACAG TTTGTACAAT GAAGGAATCC TAATTGTATG GGACCCATCT

781 GTATACCACT CAGATATCCC AAAGTGGTAC CAGAATCCGG ATTATAATTT CTTTAACAAC

841 TACAAGACTT ATCGTAAGCT GCACCCCAAT CAGCCCTTTT ACATCCTCAA GCCCCAGATG

901 CCTTGGGAGC TATGGGACAT TCTTCAAGAA ATCTCCCCAG AAGAGATTCA GCCAAACCCC

961 CCATCCTCTG GGATGCTTGG TATCATCATC ATGATGACGC TGTGTGACCA GGTGGATATT

1021 TATGAGTTCC TCCCATCCAA GCGCAAGACT GACGTGTGCT ACTACTACCA GAAGTTCTTC

1081 GATAGTGCCT GCACGATGGG TGCCTACCAC CCGCTGCTCT ATGAGAAGAA TTTGGTGAAG

1141 CATCTCAACC AGGGCACAGA TGAGGACATC TACCTGCTTG GAAAAGCCAC ACTGCCTGGC

1201 TTCCGGACCA TTCACTGCTA A (SEQ ID NO: 4)

0p-
Protein Sequence of ST6GAL1

1 MIHTNLKKKF SCCVLVFLLF AVICVWKEKK KGSYYDSFKL QTKEFQVLKS LGKLAMGSDS

61 QSVSSSSTQD PHRGRQTLGS LRGLAKAKPE ASFQVWNKDS SSKNLIPRLQ KIWKNYLSMN

121 KYKVSYKGPG PGIKFSAEAL RCHLRDHVNV SMVEVTDFPF NTSEWEGYLP KESIRTKAGP

181 WGRCAVVSSA GSLKSSQLGR EIDDHDAVLR FNGAPTANFQ QDVGTKTTIR LMNSQLVTTE

241 KRFLKDSLYN EGILIVWDPS VYHSDIPKWY QNPDYNFFNN YKTYRKLHPN QPFYILKPQM

301 PWELWDILQE ISPEEIQPNP PSSGMLGIII MMTLCDQVDI YEFLPSKRKT DVCYYYQKFF

361 DSACTMGAYH PLLYEKNLVK HLNQGTDEDI YLLGKATLPG FRTIHC (SEQ ID NO: 8)

---

The invention claimed is:

1. Recombinant human chorionic gonadotropin (hCG) comprising α2,3-sialylation, α2,6-sialylation and α2,8-sialylation.

2. Recombinant hCG according to claim 1, having a sialic acid content of 15 moles or greater of sialic acid per mole of the recombinant hCG protein.

3. Recombinant hCG according to claim 2, having a sialic acid content of from 15 to 25 moles of sialic acid per mole of the recombinant hCG protein.

4. Recombinant hCG according to claim 1, wherein 10% or more of the total sialylation of the recombinant hCG is α2,3-sialylation and/or wherein 50% or less of the total sialylation of the recombinant hCG is α2,6-sialylation.

5. Recombinant hCG according to claim 1, wherein 45% to 80% of the total sialylation of the recombinant hCG is α2,3-sialylation.

6. Recombinant hCG according to claim 1, wherein 20% to 55% of the total sialylation of the recombinant hCG is α2,6-sialylation.

7. Recombinant hCG according to claim 1, wherein the sialic acid content of the recombinant hCG is 6% or greater by mass.

8. Recombinant hCG according to claim 1, produced or expressed in a human cell line.

9. Recombinant hCG according to claim 1, produced or expressed in a PER.C6® cell line, a PER.C6® derived cell line or a modified PER.C6® cell line.

10. Recombinant hCG according to claim 8, wherein the cell line has been modified using α2,3-sialyltransferase.

11. Recombinant hCG according to claim 8, which includes α2,6-linked sialic acids (α2,6 sialylation) provided by endogenous sialyl transferase activity.

12. Recombinant hCG according to claim 1 expressed in a human cell line.

13. A pharmaceutical composition comprising recombinant hCG according to claim 1.

14. Recombinant hCG according to claim 12, comprising a sialic acid content of 15 moles or greater of sialic acid per mole of the recombinant hCG, optionally wherein 10% or more of the total sialylation is α2,3-sialylation and/or optionally wherein 50% or less of the total sialylation is α2,6-sialylation.

15. A pharmaceutical composition according to claim 13, further comprising follicle stimulating hormone (FSH) or lutenising hormone (LH) or both FSH and LH.

16. A recombinant hCG according to claim 1, comprising mono (1S), di(2S), tri(3S) and tetra(4S) sialylated structures.

17. A recombinant hCG according to claim 16, wherein the relative amounts of the sialylated structures are in the following ratios (1S:2S:3S:4S): 0.2-1:35-40:2.5-7:0.5-1.

18. A method of treatment of infertility comprising a step of administering to a subject in need of such treatment a composition comprising recombinant hCG according to claim 1.

19. A method of production of recombinant hCG according to claim 1, comprising the step of producing or expressing the recombinant hCG in a human cell line.

20. A method according to claim 19, wherein the human cell line is transfected with a vector encoding hCG alpha and beta.

21. A method according to claim 20, wherein the human cell line is transfected with a vector encoding an α2,3-sialyltrasferase.

22. A method according to claim 20, wherein the α2,3-sialyltrasferase is β-galactoside α-2,3-sialyltransferase 4.

23. A method according to claim 19, wherein the human cell line is a PER.C6® cell line, a PER.C6® derived cell line or a modified PER.C6® cell line.

24. A method according to claim 19, wherein the human cell line is a PER.C6® cell line transfected with a vector encoding hCG alpha and beta and a vector encoding an α2,3-sialyltrasferase.

25. A method according to claim 24, wherein the α2,3-sialyltrasferase is β-galactoside α-2,3-sialyltransferase 4.

* * * * *

SEQUENCE LISTING

<160> NUMBER OF SEQ ID NOS: 16

<210> SEQ ID NO 1
<211> LENGTH: 351
<212> TYPE: DNA
<213> ORGANISM: Artificial Sequence
<220> FEATURE:
<223> OTHER INFORMATION: SEQ ID 1 Nucleotide Sequence of hCG alpha

<400> SEQUENCE: 1

```
atgattact  acagaaaata  tgcagctatc  tttctggtca  cattgtcggt  gtttctgcat    60
gttctccatt  ccgctcctga  tgtgcaggat  tgcccagaat  gcacgctaca  ggaaaaccca   120
ttcttctccc  agccgggtgc  cccaatactt  cagtgcatgg  gctgctgctt  ctctagagca   180
tatcccactc  cactaaggtc  caagaagacg  atgttggtca  aaaagaacgt  cacctcagag   240
tccacttgct  gtgtagctaa  atcatataac  agggtcacag  taatgggggg  tttcaaagtg   300
gagaaccaca  cggcgtgcca  ctgcagtact  tgttattatc  acaaatctta  a            351
```

<210> SEQ ID NO 2
<211> LENGTH: 498
<212> TYPE: DNA
<213> ORGANISM: Artificial Sequence
<220> FEATURE:
<223> OTHER INFORMATION: SEQ ID 2 Nucleotide Sequence of hCG beta

<400> SEQUENCE: 2

```
atggagatgt tccaggggct gctgctgttg ctgctgctga gcatgggcgg gacatgggca      60
tccaaggagc gcttcggcc acggtgccgc cccatcaatg ccaccctggc tgtggagaag      120
gagggctgcc ccgtgtgcat caccgtcaac accaccatct gtgccggcta ctgccccacc     180
atgacccgcg tgctgcaggg ggtcctgccg gccctgcctc aggtggtgtg caactaccgc     240
gatgtgcgct tcgagtccat ccggctccct ggctgcccgc gcggcgtgaa ccccgtggtc     300
tcctacgccg tggctctcag ctgtcaatgt gcactctgcc gccgcagcac cactgactgc     360
gggggtccca aggaccaccc cttgacctgt gatgacccc gcttccagga ctcctcttcc     420
tcaaaggccc ctccccccag ccttccaagt ccatcccgac tcccggggcc ctcggacacc     480
ccgatcctcc cacaataa                                                   498
```

<210> SEQ ID NO 3
<211> LENGTH: 999
<212> TYPE: DNA
<213> ORGANISM: Artificial Sequence
<220> FEATURE:
<223> OTHER INFORMATION: SEQ ID 3 Nucleotide Sequence ST3GAL4

<400> SEQUENCE: 3

```
atgtgtcctg caggctggaa gctcctggcc atgttggctc tggtcctggt cgtcatggtg      60
tggtattcca tctcccggga agacaggtac atcgagcttt tttattttcc catcccagag     120
aagaaggagc cgtgcctcca gggtgaggca gagagcaagg cctctaagct cttttggcaac    180
tactcccggg atcagcccat cttcctgcgg cttgaggatt attctgggt caagacgcca     240
tctgcttacg agctgcccta tgggaccaag gggagtgagg atctgctcct ccgggtgcta     300
gccatcacca gctcctccat ccccaagaac atccagagcc tcaggtgccg ccgctgtgtg     360
gtcgtgggga acgggcaccg gctgcggaac agctcactgg gagatgccat caacaagtac     420
gatgtggtca tcagattgaa caatgcccca gtggctggct atgagggtga cgtgggctcc     480
aagaccacca tgcgtctctt ctaccctgaa tctgcccact cgaccccaa agtagaaaac     540
aacccagaca cactcctcgt cctggtagct ttcaaggcaa tggacttcca ctggattgag     600
accatcctga gtgataagaa gcgggtgcga aagggtttct ggaaacagcc tccctcatc     660
tgggatgtca atcctaaaca gattcggatt ctcaacccct tcttcatgga gattgcagct     720
gacaaactgc tgagcctgcc aatgcaacag ccacggaaga ttaagcagaa gcccaccacg     780
ggcctgttgg ccatcacgct ggccctccac ctctgtgact tggtgcacat gccggctt      840
ggctacccag acgcctacaa caagaagcag accattcact actatgagca gatcacgctc     900
aagtccatgg cggggtcagg ccataatgtc tcccaagagg ccctggccat taagcggatg     960
ctggagatgg gagctatcaa gaacctcacg tccttctga                            999
```

<210> SEQ ID NO 4
<211> LENGTH: 1221
<212> TYPE: DNA
<213> ORGANISM: Artificial Sequence
<220> FEATURE:
<223> OTHER INFORMATION: SEQ ID 4 Nucleotide Sequence of ST6GAL1

<400> SEQUENCE: 4

```
atgattcaca ccaacctgaa gaaaaagttc agctgctgcg tcctggtctt tcttctgttt      60
gcagtcatct gtgtgtggaa ggaaaagaag aaagggagtt actatgattc ctttaaattg     120
caaaccaagg aattccaggt gttaaagagt ctggggaaat tggccatggg gtctgattcc     180
cagtctgtat cctcaagcag cacccaggac ccccacaggg gccgccagac cctcggcagt     240
ctcagaggcc tagccaaggc caaaccgag gcctccttcc aggtgtggaa caaggacagc     300
tcttccaaaa accttatccc taggctgcaa aagatctgga gaattaccct aagcatgaac     360
aagtacaaag tgtcctacaa ggggccagga ccaggcatca agttcagtgc agaggccctg     420
cgctgccacc tccgggacca tgtgaatgta tccatggtag aggtcacaga ttttcccttc     480
aatacctctg aatgggaggg ttatctgccc aaggagagca ttaggaccaa ggctgggcct     540
tggggcaggt gtgctgttgt gtcgtcagcg ggatctctga agtcctccca actaggcaga     600
gaaatcgatg atcatgacgc agtcctgagg tttaatgggg cacccacagc caacttccaa     660
caagatgtgg gcacaaaaac taccattcgc ctgatgaact ctcagttggt taccacagag     720
aagcgcttcc tcaaagacag tttgtacaat gaaggaatcc taattgtatg ggaccccatct     780
gtataccact cagatatccc aaagtggtac cagaatccgg attataattt ctttaacaac     840
tacaagactt atcgtaagct gcaccccaat cagccctttt acatcctcaa gccccagatg     900
ccttgggagc tatgggacat tcttcaagaa atctccccag aagagattca gccaaacccc     960
ccatcctctg ggatgcttgg tatcatcatc atgatgacgc tgtgtgacca ggtggatatt    1020
tatgagttcc tcccatccaa gcgcaagact gacgtgtgct actactacca gaagttcttc    1080
gatagtgcct gcacgatggg tgcctaccac ccgctgctct atgagaagaa tttggtgaag    1140
catctcaacc agggcacaga tgaggacatc tacctgcttg aaaagccac actgcctggc     1200
ttccggacca ttcactgcta a                                                1221
```

<210> SEQ ID NO 5
<211> LENGTH: 129
<212> TYPE: PRT
<213> ORGANISM: Artificial Sequence
<220> FEATURE:
<223> OTHER INFORMATION: Protein Sequence of hCG alpha

<400> SEQUENCE: 5

```
Met Lys Thr Leu Gln Phe Phe Phe Leu Phe Cys Cys Trp Lys Ala Ile
  1               5                  10                  15

Cys Cys Asn Ser Cys Glu Leu Thr Asn Ile Thr Ile Ala Ile Glu Lys
             20                  25                  30

Glu Glu Cys Arg Phe Cys Ile Ser Ile Asn Thr Thr Trp Cys Ala Gly
         35                  40                  45

Tyr Cys Tyr Thr Arg Asp Leu Val Tyr Lys Asp Pro Ala Arg Pro Lys
     50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                 85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu
```

<210> SEQ ID NO 6
<211> LENGTH: 165
<212> TYPE: PRT
<213> ORGANISM: Artificial Sequence
<220> FEATURE:
<223> OTHER INFORMATION: Protein Sequence of hCG beta

<400> SEQUENCE: 6

```
Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
            85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Ser Lys Ala Pro
            130                 135                 140

Pro Pro Ser Leu Pro Ser Pro Ser Arg Leu Pro Gly Pro Ser Asp Thr
145                 150                 155                 160

Pro Ile Leu Pro Gln
                165
```

<210> SEQ ID NO 7
<211> LENGTH: 332
<212> TYPE: PRT
<213> ORGANISM: Artificial Sequence
<220> FEATURE:
<223> OTHER INFORMATION: Protein Sequence of ST3GAL4

<400> SEQUENCE: 7

```
Met Cys Pro Ala Gly Trp Lys Leu Leu Ala Met Leu Ala Leu Val Leu
1               5                   10                  15

Val Val Met Val Trp Tyr Ser Ile Ser Arg Glu Asp Arg Tyr Ile Glu
            20                  25                  30

Leu Phe Tyr Phe Pro Ile Pro Glu Lys Lys Glu Pro Cys Leu Gln Gly
            35                  40                  45

Glu Ala Glu Ser Lys Ala Ser Lys Leu Phe Gly Asn Tyr Ser Arg Asp
    50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
                85                  90                  95

Leu Arg Val Leu Ala Ile Thr Ser Ser Ser Ile Pro Lys Asn Ile Gln
            100                 105                 110

Ser Leu Arg Cys Arg Arg Cys Val Val Val Gly Asn Gly His Arg Leu
            115                 120                 125
```

```
Arg Asn Ser Ser Leu Gly Asp Ala Ile Asn Lys Tyr Asp Val Val Ile
130                 135                 140

Arg Leu Asn Asn Ala Pro Val Ala Gly Tyr Glu Gly Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
                180                 185                 190

Ala Met Asp Phe His Trp Ile Glu Thr Ile Leu Ser Asp Lys Lys Arg
            195                 200                 205

Val Arg Lys Gly Phe Trp Lys Gln Pro Pro Leu Ile Trp Asp Val Asn
210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
                260                 265                 270

Asp Leu Val His Ile Ala Gly Phe Gly Tyr Pro Asp Ala Tyr Asn Lys
            275                 280                 285

Lys Gln Thr Ile His Tyr Tyr Glu Gln Ile Thr Leu Lys Ser Met Ala
290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330

<210> SEQ ID NO 8
<211> LENGTH: 406
<212> TYPE: PRT
<213> ORGANISM: Artificial Sequence
<220> FEATURE:
<223> OTHER INFORMATION: Protein Sequence of ST6GAL1

<400> SEQUENCE: 8

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
                20                  25                  30

Ser Tyr Tyr Asp Ser Phe Lys Leu Gln Thr Lys Glu Phe Gln Val Leu
            35                  40                  45

Lys Ser Leu Gly Lys Leu Ala Met Gly Ser Asp Ser Gln Ser Val Ser
50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
130                 135                 140

Arg Asp His Val Asn Val Ser Met Val Glu Val Thr Asp Phe Pro Phe
145                 150                 155                 160
```

Asn Thr Ser Glu Trp Glu Gly Tyr Leu Pro Lys Glu Ser Ile Arg Thr
            165                 170                 175

Lys Ala Gly Pro Trp Gly Arg Cys Ala Val Val Ser Ser Ala Gly Ser
        180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Tyr Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
            405

<210> SEQ ID NO 9
<211> LENGTH: 39
<212> TYPE: DNA
<213> ORGANISM: Artificial Sequence
<220> FEATURE:
<223> OTHER INFORMATION: PCR Primer CGa-fw

<400> SEQUENCE: 9
ccaggatccg ccaccatgga ttactacaga aaaatatgc                          39

<210> SEQ ID NO 10
<211> LENGTH: 31
<212> TYPE: DNA
<213> ORGANISM: Artificial Sequence
<220> FEATURE:
<223> OTHER INFORMATION: PCR Primer CGa-rev

<400> SEQUENCE: 10
ggatggctag cttaagattt gtgataataa c                                  31

<210> SEQ ID NO 11
<211> LENGTH: 36
<212> TYPE: DNA
<213> ORGANISM: Artificial Sequence
<220> FEATURE:
<223> OTHER INFORMATION: PCR Primer CGb-fw

```
<400> SEQUENCE: 11
ccaggcgcgc caccatggag atgttccagg ggctgc                                36

<210> SEQ ID NO 12
<211> LENGTH: 30
<212> TYPE: DNA
<213> ORGANISM: Artificial Sequence
<220> FEATURE:
<223> OTHER INFORMATION: PCR Primer CGb-rev

<400> SEQUENCE: 12
ccgggttaac ttattgtggg aggatcgggg                                        30

<210> SEQ ID NO 13
<211> LENGTH: 37
<212> TYPE: DNA
<213> ORGANISM: Artificial Sequence
<220> FEATURE:
<223> OTHER INFORMATION: PCR Primer 2,3STfw

<400> SEQUENCE: 13
ccaggatccg ccaccatgtg tcctgcaggc tggaagc                               37

<210> SEQ ID NO 14
<211> LENGTH: 35
<212> TYPE: DNA
<213> ORGANISM: Artificial Sequence
<220> FEATURE:
<223> OTHER INFORMATION: PCR Primer 2,3STrev

<400> SEQUENCE: 14 ttttttctt aagtcagaag gacgtgaggt tcttg                                  35

<210> SEQ ID NO 15
<211> LENGTH: 36
<212> TYPE: DNA
<213> ORGANISM: Artificial Sequence
<220> FEATURE:
<223> OTHER INFORMATION: PCR Primer 2,6STfw

<400> SEQUENCE: 15
ccaggatccg ccaccatgat tcacaccaac ctgaag                                36

<210> SEQ ID NO 16
<211> LENGTH: 32
<212> TYPE: DNA
<213> ORGANISM: Artificial Sequence
<220> FEATURE:
<223> OTHER INFORMATION: PCR Primer 2,6STrev

<400> SEQUENCE: 16 ttttttctt aagttagcag tgaatggtcc gg                                     32
```